(12) United States Patent
Pazenok

(10) Patent No.: US 7,317,105 B2
(45) Date of Patent: Jan. 8, 2008

(54) PREPARATION OF 4-HALOALKYLNICOTINAMIDES

(75) Inventor: Sergiy Pazenok, Solingen (DE)

(73) Assignee: Bayer Cropscience AG, Monheim (DE)

( * ) Notice: Subject to any disclaimer, the term of this patent is extended or adjusted under 35 U.S.C. 154(b) by 576 days.

(21) Appl. No.: 10/515,507

(22) PCT Filed: May 9, 2003

(86) PCT No.: PCT/EP03/04869

§ 371 (c)(1),
(2), (4) Date: Nov. 24, 2004

(87) PCT Pub. No.: WO03/099791

PCT Pub. Date: Dec. 4, 2003

(65) Prior Publication Data

US 2005/0176734 A1    Aug. 11, 2005
US 2006/0100217 A9    May 11, 2006

(30) Foreign Application Priority Data

May 24, 2002   (DE) ................ 102 23 274

(51) Int. Cl.
*C07D 213/08*     (2006.01)
(52) U.S. Cl. .................................... 546/317
(58) Field of Classification Search ........... 546/317
See application file for complete search history.

(56) References Cited

U.S. PATENT DOCUMENTS

| 6,239,160 B1 | 5/2001 | Tiebes et al. |
| 6,541,640 B2 | 4/2003 | Pazenok et al. |
| 2004/0167334 A1 | 8/2004 | Shermolovich et al. |

FOREIGN PATENT DOCUMENTS

| EP | 0 580 374 A1 | 1/1994 |
| EP | 0 744 400 A2 | 11/1996 |
| WO | 01/70692 A2 | 9/2001 |
| WO | 02/48111 A2 | 6/2002 |
| WO | 03/044013 A1 | 5/2003 |

OTHER PUBLICATIONS

International Preliminary Examination Report for PCT/EP2003/004869, Sep. 17, 2004 (cited by Applicants on Jun. 10, 2005).*

* cited by examiner

*Primary Examiner*—Zinna N. Davis
(74) *Attorney, Agent, or Firm*—Buchanan, Ingersoll & Rooney, PC

(57) ABSTRACT

The invention relates to a method for producing 4-haloalkylnicotinamides having the formula (I):

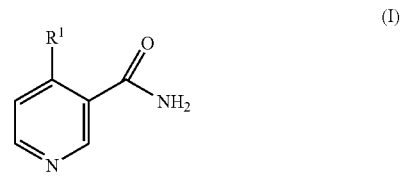

wherein $R^1$ is $(C_1\text{-}C_4)$haloalky, comprising subjecting one or more 3-(($C_1\text{-}C_4$)haloalkyl-3-oxo-1-alkenylamino)nitriles of the formula (II), (III) or (IV):

$$R^1\text{—C(O)—CH=CH—NH—CH=CH—CN} \quad (II)$$

$$R^1\text{—C(O)—CH=CH—NH—CH(ZR}^2\text{)—CH}_2\text{—CN} \quad (III)$$

$$R_1\text{—C(O)—CH=CH—NH—CH(Hal)—CH}_2\text{—CN} \quad (IV)$$

where $R^1$ is as defined above, $R^2$ is the same or different and is $(C_1\text{-}C_6)$-alkyl and Z is the same or different and is O, S or $NR^1$, to a ring-closing reaction and simultaneous hydrolysis in the presence of a strong acid.

18 Claims, No Drawings

PREPARATION OF 4-HALOALKYLNICOTINAMIDES

CROSS-REFERENCE TO RELATED APPLICATIONS

This application is the U.S. national stage of International Appln. No. PCT/EP03/04869, filed May 9, 2003, and claims priority under 35 U.S.C. § 119(a)-(d) of German Patent Application No.10223274.1, filed May 24, 2002, said applications being incorporated by reference herein in their entireties and relied upon.

The present invention relates to a process for preparing 4-haloalkyinicotinamides.

4-Haloalkylnicotinamides are useful starting materials for preparing pesticides, as described, for example, in WO-A 98/57 969, EP-A 0 580 374 and WO-A 01/70692.

These compounds can be prepared in two stages from 4-haloalkylnicotinic acids whose synthesis is described, for example, in EP-A 0 744 400, or by hydrolysis of 4-haloalkylnicotinonitriles, see, for example, WO-A 02/048111.

Surprisingly, a simple process has now been found for preparing 4-haloalkylnicotinamides, especially trifluoromethyinicotinamide, by cyclization and hydrolysis of 3-(haloalkyl-3-oxo-1-butenylamino)acrylonitriles in the presence of a strong acid.

The invention therefore provides a process for preparing 4-haloalkylnicotinamides of the formula (I)

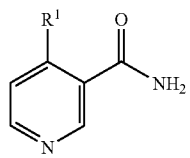

(I)

where
R$^1$ is (C$_1$-C$_4$)-haloalkyl, which comprises subjecting
one or more 3-((C$_1$-C$_4$)-haloalkyl-3-oxo-1-alkenylamino) nitriles of the formula (II), (III) and/or (IV)

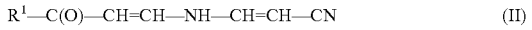

R$^1$—C(O)—CH=CH—NH—CH=CH—CN (II)

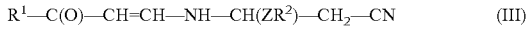

R$^1$—C(O)—CH=CH—NH—CH(ZR$^2$)—CH$_2$—CN (III)

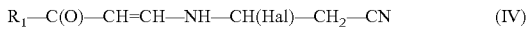

R$_1$—C(O)—CH=CH—NH—CH(Hal)—CH$_2$—CN (IV)

where
R$^1$ is as defined above;
R$^2$ is the same or different and is (C$_1$-C$_6$)-alkyl and
Z is the same or different and is O, S or NR$^1$, to a ring-closing reaction and simultaneous hydrolysis in the presence of a strong acid.

The process according to the invention enables the preparation of the nicotinamide derivatives (I) from the nitrile derivatives (II-IV) in only one step and is additionally particularly simple to carry out. This is particularly surprising because it is known that the hydrolysis of 4-trifluoromethylnicotinonitrile to the amide is only achieved by heating to 120-140° C. for 8 h in concentrated H$_2$SO$_4$.

"(C$_1$-C$_4$)-Haloalkyl" is an alkyl group in which one or more hydrogen atoms are replaced by the same number of identical or different halogen atoms, preferably chlorine or fluorine, such as the trifluoromethyl, the 1-fluoroethyl, the 2,2,2-trifluoroethyl, the chloromethyl, the fluoromethyl, the difluoromethyl and the 1,1,2,2-tetrafluoroethyl group.

The symbols in the formulae (I) to (IV) are preferably defined as follows:
R$^1$ is preferably CF$_2$H, CFCl$_2$, CF$_2$Cl, CF$_3$, C$_2$F$_5$ or C$_3$F$_7$, more preferably CF$_3$.
R$^2$ is preferably (C$_1$-C$_4$)-alkyl, such as methyl, ethyl, n-propyl, isopropyl, n-butyl, isobutyl, t-butyl, more preferably methyl or ethyl, most preferably methyl.
Z is preferably O or NR$^1$.
Hal is F, Cl, Br or I, preferably Cl or Br.

The starting materials, 3-(haloalkyl-3-oxo-1-alkenylamino)acrylonitrile derivatives (II) or enamines of the formulae (III) and (IV), are known and can be prepared, for example, as described in WO-A 02/048111.

The cyclization to the 4-haloalkylnicotinamides (I) takes place in the presence of a strong acid, preferably having a pK$_a$ value of below 0.5. During the cyclization in the strongly acidic medium, the transformation of the nitrile group also takes place.

Particularly preferred acids are H$_2$SO$_4$, SO$_3$, oleum, phosphoric acid, polyphosphoric acids, perfluoroalkanesulfonic acids, such as trifluoromethylsulfonic acid, methanesulfonic acid and p-toluenesulfonic acid, and very particular preference is given to H$_2$SO$_4$ and polyphosphoric acid, special preference to H$_2$SO$_4$.

It is also possible to use acid mixtures.

Depending on the compound, acid and further reaction conditions used, the ratio of the compound(s) (II), (III) and/or (IV) to acid can vary within a wide range.

In general, the amount of acid used is from 4 to 30 parts by weight, preferably from 6 to 15 parts by weight, per part by weight of compound (II)-(IV).

Depending on the compound used and other reaction conditions, the reaction temperature can vary within wide limits. In general, it is in the range from 0° C. to +40° C., and the reaction time is typically from 0.1 to 6 h, preferably from 3 to 5 h.

The reaction conditions also vary in a manner familiar to those skilled in the art, depending on whether a compound of the formula (II), (III) or (IV) is used.

The reaction can be carried out in a solvent. The components (II-IV) and the acid can be initially charged separately in the solvent and these solutions/suspensions reacted together, or one of the components is initially charged in the solvent and the other component is added.

Preferred solvents are halogenated hydrocarbons such as methylene chloride or chloroform, ethers such as diethyl ether or diisopropyl ether, and SO$_2$. The amount of solvent used can vary within wide limits and depends, for example, on which starting material is used. It is generally up to 30 parts by weight, preferably from 6 to 15 parts by weight, per part by weight of compound (II)-(IV).

The workup can be effected by known methods familiar to those skilled in the art, for example by dilution with water and filtration or extraction of the product.

Depending on the nature of the cyclization reagent (e.g. SO$_3$, oleum, concentrated H$_2$SO$_4$), aqueous workup is strictly necessary to release the amide from its precursor, if necessary, and to isolate it.

The compound (I), in particular 4-trifluoromethylnicotinamide, finds use, for example, as an intermediate in the preparation of crop protection agents, in particular pesticides, such as insecticides.

It is particularly suitable for further conversion to compounds, as described in WO-A 98/57969, EP-A 0 580 374 and WO-A 01/07692. These documents, in particular the compounds of the formula (I) in each case and the exemplary embodiments, are explicitly incorporated herein by reference.

The invention also provides a process for preparing insecticidally active 4-haloalkylnicotinic acid derivatives, in particular 4-trifluoromethylnicotinic acid derivatives, according to WO-A 98/57969, EP-A 0 580 374 and/or WO-A 01/70692, by preparing the above-described compounds of the formula (I), subjecting these to a ring-closing reaction, optionally hydrolyzing them and further reacting them by processes described in the documents cited to give the insecticidally active end compounds.

The content of German patent application 102 23 274.1, from which this application claims priority, and of the enclosed abstract is hereby incorporated by reference.

The invention is illustrated by the examples which follow, without being limited by them.

EXAMPLE NO. 1

4-Trifluoromethylnicotinamide

A three-neck flask was initially charged under $N_2$ with 100 ml of $H_2SO_4$ (d 1.8) and the solution was cooled to 10° C.

30 g (0.5 mol) of N-(2-cyanovinyl)-4,4,4-trifluoro-3-keto-1-butenylamine were added at this temperature within 1 h.

Subsequently, the mixture was stirred at room temperature (RT) for 3-5 h. The reaction mixture was added to 300 g of ice, the pH adjusted to 3-4 using 40% by weight NaOH and the product extracted using ethyl acetate. The solvent was removed under reduced pressure.

27 g (90%) of the amide were obtained, m.p.: 166-167° C. $^{19}F$ NMR δ: −60.0 (singlet) ppm.

EXAMPLE NO. 2

4-Trifluoromethylnicotinamide

The procedure of example 1 was repeated, except using polyphosphoric acid instead of $H_2SO_4$. The reaction mixture was heated to 40° C. for 4 h and 24 g (80%) of the product having a melting point of 165° C. were obtained.

EXAMPLE NO. 3

4-Difluoromethylnicotinamide

The procedure of example 1 was repeated, except that N-(2-cyanovinyl)-4,4-difluoro-3-keto-1-butenylamine was used instead of N-(2-cyanovinyl)-4,4,4-trifluoro-3-keto-1-butenylamine.

Yield 65%. m.p.: 124-125° C.

The invention claimed is:

1. A process for preparing 4-haloalkylnicotinamides of the formula (I)

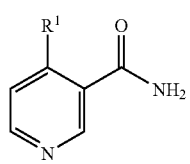

(I)

where
$R^1$ is $(C_1\text{-}C_4)$-haloalkyl,
which comprises subjecting
one or more 3-(($C_1$-$C_4$-haloalkyl-3-oxo-1-alkenylamino) nitriles of the formula (II), (III) and/or (IV)

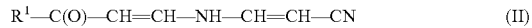 (II)

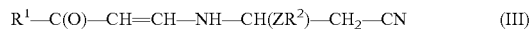 (III)

 (IV)

where
$R^1$ is as defined above;
$R^2$ is the same or different and is $(C_1\text{-}C_6)$-alkyl and
Z is the same or different and is O, S or $NR^1$,
to a ring-closing reaction and simultaneous hydrolysis in the presence of a strong acid having a $pK_a$ value of below 0.5.

2. The process as claimed in claim 1, wherein $R^1$ in the formula (I) is $CF_2H$, $CFCl_2$, $CF_2Cl$, $CF_3$, $C_2F_5$ or $C_3F_7$.

3. The process as claimed in claim 2, wherein $R^1$ in the formula (I) is $CF_3$.

4. The process as claimed in claim 1, carried out in the presence of one or more acids selected from the group consisting of $H_2SO_4$, $SO_3$, oleum, phosphoric acid, polyphosphoric acids, perfluoroalkanesulfonic acids, methanesulfonic acid and p-toluenesulfonic acid.

5. The process as claimed in claim 4, carried out in the presence of $H_2SO_4$.

6. The process as claimed in claim 1, carried out in a solvent.

7. The process as claimed in claim 2, carried out in the presence of one or more acids selected from the group consisting of $H_2SO_4$, $SO_3$, oleum, phosphoric acid, polyphosphoric acids, perfluoroalkanesulfonic acids, methanesulfonic acid and p-toluenesulfonic acid.

8. The process as claimed in claim 3, carried out in the presence of one or more acids selected from the group consisting of $H_2SO_4$, $SO_3$, oleum, phosphoric acid, polyphosphoric acids, perfluoroalkanesulfonic acids, methanesulfonic acid and p-toluenesulfonic acid.

9. The process as claimed in claim 7, carried out in the presence of $H_2SO_4$.

10. The process as claimed in claim 8, carried out in the presence of $H_2SO_4$.

11. The process as claimed in claim 2, wherein the reaction is carried out in a solvent.

12. The process as claimed in claim 3, wherein the reaction is carried out in a solvent.

13. The process as claimed in claim 4, wherein the reaction is carried out in a solvent.

14. The process as claimed in claim 5, wherein the reaction is carried out in a solvent.

15. The process as claimed in claim 7, wherein the reaction is carried out in a solvent.

16. The process as claimed in claim 8, wherein the reaction is carried out in a solvent.

17. The process as claimed in claim 9, wherein the reaction is carried out in a solvent.

18. The process as claimed in claim 10, wherein the reaction is carried out in a solvent.

* * * * *